United States Patent [19]

Korte et al.

[11] 4,025,536

[45] May 24, 1977

[54] TRI-CYCLIC COMPOUNDS DERIVED FROM THIAPHLOROGLUCINOL ETHERS

[75] Inventors: Friedrich-Wilhelm A. G. K. Korte, Attenkirchen, Germany; Frederick Coulston, Rensselaer, N.Y.

[73] Assignee: Abbott Laboratories, North Chicago, Ill.

[22] Filed: Sept. 5, 1975

[21] Appl. No.: 610,602

[52] U.S. Cl. .............................. 260/345.3; 424/283
[51] Int. Cl.² ..................................... C07D 307/83
[58] Field of Search .................................. 260/345.3

[56] References Cited

UNITED STATES PATENTS

| 3,388,136 | 6/1968 | Taylor et al. | 260/345.3 |
| 3,507,885 | 4/1970 | Fahrenholtz | 260/345.3 |

*Primary Examiner*—Bernard Helfin
*Assistant Examiner*—Nicky Chan

*Attorney, Agent, or Firm*—Vincent A. Mallare; Robert L. Niblack

[57] ABSTRACT

This invention provides novel benzopyran derivatives of the formula

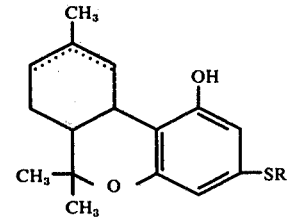

wherein R is an alkyl group of 3–10 carbon atoms.

The compounds of this invention are useful as antihypertensive agents.

9 Claims, No Drawings

TRI-CYCLIC COMPOUNDS DERIVED FROM THIAPHLOROGLUCINOL ETHERS

DESCRIPTION OF THE INVENTION

This invention relates to novel tri-cyclic compounds derived from phloroglucinol and the processes of producing the same. More particularly, this invention is concerned with tri-cyclic compounds having pharmacological activity such as antihypertensive activity.

According to the present invention, these are tri-cyclic compounds of the formula

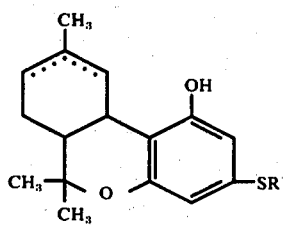

wherein R is an alkyl group of 3 to 10 carbon atoms.

As used herein, the term "alkyl" means saturated monovalent aliphatic radicals, including straight and branched chain radicals of from 3 to 10 carbon atoms, as illustrated by, but not limited to n-butyl, n-octyl, isopentyl and the like.

The compounds of the present invention are useful as antihypertensive agents and provide such activity in dosages of from 3 to 50 mg./kg. of body weight daily.

The compounds of the present invention can generally be prepared by heating under reflux a thiaphloroglucinol ether with trans-p-menthadiene-(2,8)-ol-(1) in the presence of p-toluene sulphonic acid in benzene. After the refluxed ether combination is cooled, water is added to the mixture and the acid is removed by repeated extraction with water. After drying by $Na_2SO_4$ and evaporation, the final product is obtained by column chromatography on silica with benzene-cyclohexane solvent.

This preparation is represented by the following:

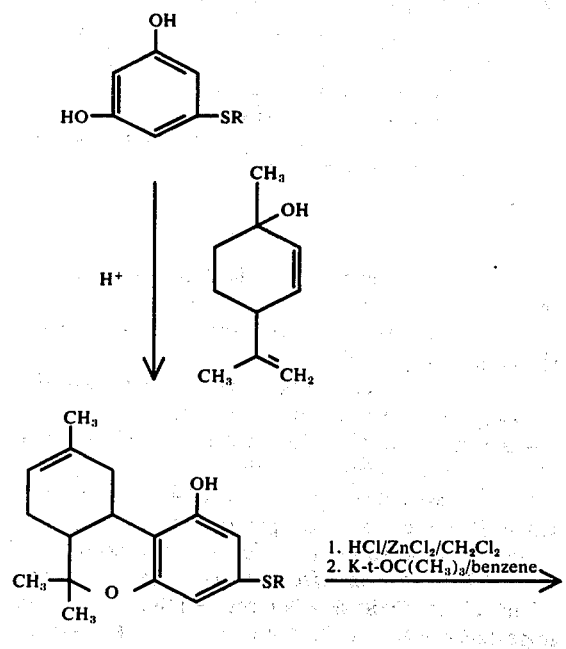

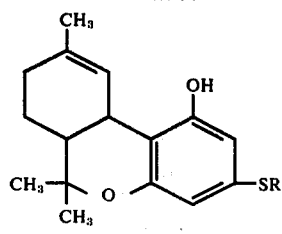

Some of the ultimate products that can be produced according to the general process of the present invention are 3-n-butylthio-6a,7,10,10a-tetrahydro-6,6,9-trimethyl-6H-dibenzo[b,d]pyran-1-ol of the formula 3-n-butylthio-6a,7,8,10a-tetrahydro-6,6,9-trimethyl-6H-dibenzo[b,d]pyran-1-ol of the formula 3-n-octylthio-6a,7,10,10a-tetrahydro-6,6,9-trimethyl-6H-dibenzo[b,d]pyran-1-ol of the formula 3-n-octylthio-6a,7,8,10a-tetrahydro-6,6,9-trimethyl-6H-dibenzo[b,d]pyran-1-ol of the formula 3-isopentylthio,6a,7,10,10a-tetrahydro-6,6,9-trimethyl-6H-dibenzo[b,d]pyran-1-ol of the formula

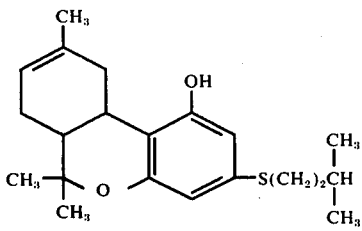

The amount of active ingredient administered may be varied; however, it is necessary that the amount of active ingredient be such that a suitable dosage is given. The selected dosage depends on the desired therapeutic effect, on the route of administration and on the duration of treatment. Dosages of from 3 to 50 mg./kg. of body weight daily, preferably in divided dosages, i.e., 2 to 3 times daily, can be administered.

The active agents of this invention can be administered to animals, including humans, as pure compounds. It is advisable however, to first combine one or more of the compounds with a suitable pharmaceutical carrier to obtain a satisfactory size to dosage relationship and thereby obtain a pharmaceutical composition.

Pharmaceutical carriers which are liquid or solid, can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Flavoring and sweetening agents and other therapeutically inert ingredients necessary in the formulation of the desired tablets can also be included.

The compounds of this invention exhibit both oral and parenteral activity and accordingly can be formulated in dosage forms for either oral or parenteral administration to a patient.

The following examples further illustrate this invention without, however, limiting it thereto.

EXAMPLE 1

Synthesis of
3-n-butylthio-6a,7,10,10a-tetrahydro-6,6,9-trimethyl-6H-dibenzo[b,d]pyran-1-ol 1.98 grams (10.00 mmoles) of phloroglucinol-monobutylthio-ether is refluxed for 4 hours with 1.8 grams (12.0 mmoles) of (+)-trans-p-menthadiene-(2,8)-ol-(1) in the presence of 1.0 gram of p-toluenesulfonic acid hydrate in 25 ml. of benzene. After this mixture is cooled to room temperature, water is added, and the acid is removed by repeated extraction with water.

The organic solution is dried with $MgSO_4$ and then evaporated. The final product is obtained upon column-chromatography on silica with benzene/cyclohexane solvent.

The yield is 1.1 grams (35%).

EXAMPLE 2

Synthesis of
3-n-butylthio-6a,7,8,10a-tetrahydro-6,6,9-trimethyl-6H-dibenzo/b,d/pyran-1-ol 1.5 grams (5 mmoles) of the end product of Example 1 are dissolved in 50 ml. $CH_2Cl_2$ to which are added 0.7 grams (5 mmoles) of $ZnCl_2$. Thereafter, HCl-gas is allowed to pass for one hour through the solution under ice-cooling and then it is allowed to stand over-night. Ice-water is added until zinc-hydroxide begins to precipitate. The methylene chloride phase is dried after separation and evaporated under vacuum. The remaining product is dissolved in 40 ml. benzene and is treated with 2.3 grams (20 mmoles) potassium t-butylate at 0°. The solvent is then heated at 60°-70° with stirring for 30 minutes followed by ice cooling and saturation with $CO_2$-gas. This is followed by the addition of benzene. The solution is then shaken with aqueous $NaHCO_3$-solution. The benzene extracts are dried and evaporated under vacuum. The residue is chromatographed on silica gel in benzene/cyclohexane system. The yield is 1.1 grams (72%) of a transparent, viscous oil, which easily darkens in air (oxidation) and should be stored under nitrogen.

EXAMPLE 3

Determination of antihypertensive activity in SH rats

Male SH rats were trained to be restrained in a wire mesh cylinder in a warming box for at least 2 times before being tested.

The rats were warmed for about ½ hour prior to blood pressure measurement.

The warming box was maintained at a constant temperature of 35° C.

An occluding cuff, attached to a programmed sphygmomanometer, was placed near the base of the tail of each rat and the pressure in the cuff was increased automatically from zero to 250 mm Hg at a rate of 10 mm Hg per second. The total time for each cycle of inflation and deflation of the cuff was 50 seconds and the interval between cycles was 1 minute.

A photocell was placed distal to the cuff to pick up the pulses due to forward motion of blood flow with each heart beat. As the pressure in the cuff increased, the pulse disappeared completely at a point where cuff pressure equals or exceeds the arterial blood pressure, and it reappeared during deflation at approximately the same pressure. Five good (interference free) signals for deflation were recorded for each rat. Rats with blood pressure of 180 mm Hg or more during the control period were used in this study,.

A model 7 Grass polygraph was used to record the blood pressure and heart rate of the rats. Control and various interval readings were taken.

All compounds were administered orally in a fine suspension of physiological saline to two to four rats each. The compounds administered to the rats included:

Compounds 1. 3-n-butylthio-6a,7,10,10a-tetrahydro-6,6,9-trimethyl-6H-dibenzo[b,d]pyran-1-ol.
2. 3-n-butylthio-6a,7,8,10a-tetrahydro-6,6,9-trimethyl-6H-dibenzo[b,d]pyran-1-ol.
3. 3-n-octylthio-6a,7,10,10a-tetrahydro-6,6,9-trimethyl-6H-dibenzo[b,d]pyran-1-ol.
4. 3-n-octylthio-6a,7,8,10a-tetrahydro-6,6,9-trimethyl-6H-dibenzo[b,d]pyran-1-ol.
5. 3-n-isopenthylthio-6a,7,10,10a-tetrahydro-6,6,9-trimethyl-6H-dibenzo[b,d]pyran-1-ol.

The blood pressure (systolic) was measured at intervals of 3 to 24 hours after the drug was administered.

The effect on the blood pressure in the spontaneously hypertensive SH rats is shown in the Table below:

TABLE I

EFFECT ON BLOOD PRESSURE IN SPONTANEOUSLY HYPERTENSIVE (SH) RATS (ORAL ADMINISTRATION)

| Compound | Oral Dose (mg/kg) | Control Blood Pressure (mm Hg) | Per Cent Change in Blood Pressure | |
|---|---|---|---|---|
| | | | 3 Hour | 24 Hour |
| $\Delta^8$ —S(CH$_2$)$_3$CH$_3$ | 10 | 226 | −29 | −3 |
| | | 203 | −2 | −6 |
| | | 201 | −26 | −10 |
| | | 204 | −24 | −9 |
| | 30 | 200 | −31 | −1 |
| | | 189 | −15 | −10 |
| | | 198 | −22 | −8 |
| | | 198 | −22 | −6 |

As can be seen in the results provided in Table I, the compounds of the present invention are active as antihypertensive agents and can be used effectively to reduce the blood pressure in animals.

It is to be understood that the foregoing description has been given only to provide a clear understanding of the embodiments of the present invention. Accordingly, the foregoing description is not intended to limit the scope of the present invention as set forth in the appended claims, and no unnecessary limitations should be understood therefrom, as modifications will be obvious to those skilled in the art.

What is claimed is:

1. A compound of the formula

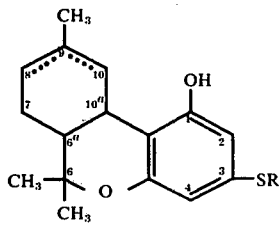

wherein R is an alkyl group of 3 to 10 carbon atoms and the dotted line indicates a double bond connected to the 9-position.

2. A compound according to claim 1, wherein R is butyl.

3. A compound according to claim 2, 3-n-butylthio-6a,7,10,10a-tetrahydro-6,6,9-trimethyl-6H-dibenzo[b,d]pyran-1-ol.

4. A compound according to claim 2, 3-n-butylthio-6a,7,8,10a-tetrahydro-6,6,9-trimethyl-6H-dibenzo[b,d]pyran-1-ol.

5. A compound according to claim 1, wherein R is octyl.

6. A compound according to claim 5, 3-n-octylthio-6a,7,10,10a-tetrahydro-6,6,9-trimethyl-6H-dibenzo[b,d]pyran-1-ol.

7. A compound according to claim 5, 3-n-octylthio-6a,7,8,10a-tetrahydro-6,6,9-trimethyl-6H-dibenzo[b,d]pyran-1-ol.

8. A compound according to claim 1 wherein R is isopentyl.

9. A compound according to claim 8, 3-isopentylthio-6a,7,10,10a-tetrahydro-6,6,9-trimethyl-6H-dibenzo[b,d]pyran-1-ol.

* * * * *